(12) United States Patent
Radmacher et al.

(10) Patent No.: US 6,602,717 B2  
(45) Date of Patent: Aug. 5, 2003

(54) APPARATUS FOR ELIMINATING HALIDE IONS FROM AQUEOUS SOLUTIONS AND METHOD TO REMOVE HALIDE IONS FROM LIQUID AQUEOUS SAMPLES

(75) Inventors: Edmund Radmacher, Düren (DE); Markus John, Anröchte (DE); Dirk Reinhardt, Düren (DE); Klaus Möller, Eschweiler (DE)

(73) Assignee: Macherey-Nagel GmbH & Co. KG, Duren (DE)

( * ) Notice: Subject to any disclaimer, the term of this patent is extended or adjusted under 35 U.S.C. 154(b) by 33 days.

(21) Appl. No.: 09/912,044

(22) Filed: Jul. 24, 2001

(65) Prior Publication Data

US 2002/0017460 A1 Feb. 14, 2002

(30) Foreign Application Priority Data

Aug. 2, 2000 (DE) .................... 200 13 290 U

(51) Int. Cl.[7] .................................. G01N 1/34
(52) U.S. Cl. .............. 436/175; 436/62; 436/124; 436/125; 436/177; 436/178; 422/69; 422/70; 422/79; 422/101
(58) Field of Search ................ 422/69, 70, 79, 422/100, 101; 436/62, 124, 125, 175, 177, 178

(56) References Cited

U.S. PATENT DOCUMENTS

| 4,341,635 A | * | 7/1982 | Golias |
| 5,042,502 A | * | 8/1991 | Guirguis |
| 5,266,193 A | | 11/1993 | Kimura et al. |
| 5,378,359 A | * | 1/1995 | Huse et al. |
| 5,667,754 A | | 9/1997 | Brayton et al. |
| 5,683,914 A | | 11/1997 | Miller et al. |

FOREIGN PATENT DOCUMENTS

| JP | 59-190657 | 10/1984 |
| JP | 60-100049 | 6/1985 |
| JP | 02-236166 | 9/1990 |

OTHER PUBLICATIONS

DIN 38414–20—German standard methods for the examination of water, waste water and sludge, Jan. 1996.
DIN 38409 (Part 41, 43, and 44) German standard methods for examination of water, waste water and sludge, Dec. 1980.

* cited by examiner

Primary Examiner—Jan Ludlow
(74) Attorney, Agent, or Firm—Baker & Daniels

(57) ABSTRACT

Apparatus for eliminating halide ions such as chloride ions from aqueous solutions having a hollow cylindrical sample holding chamber (2), the front end of which has an orifice (3) and in the vicinity of which is disposed a filter plate (4) that extends over the cross section of the sample holding chamber (2) and is liquid-permeable and essentially impermeable for solids and is inserted in a fixed manner into the hollow cylinder; a plunger (6) which can move to and fro in the sample holding chamber (2) and has a plunger stem (7) attached thereto engages in the open rear end (5) of the sample holding chamber, and, in the sample holding chamber (2) between the filter plate (4) and the plunger (6) is disposed a freely movable bed (7) of an adsorbent reacting with halide ions and forming a sparingly soluble compound, which bed fills a part of the sample holding chamber (2). The adsorbent is preferably charged with silver nitrate as compound reactive with halide ions.

21 Claims, 1 Drawing Sheet

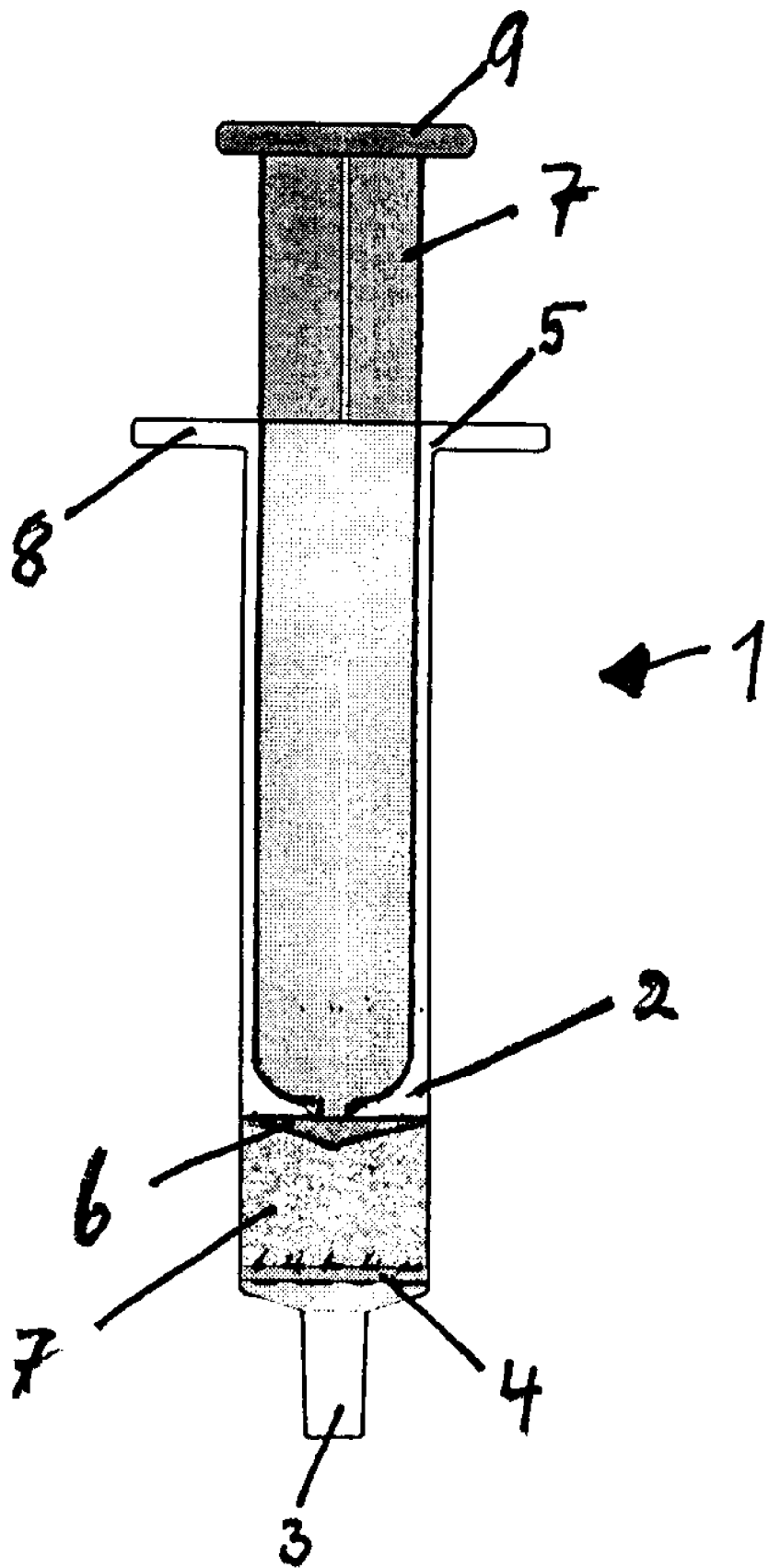

APPARATUS FOR ELIMINATING HALIDE IONS FROM AQUEOUS SOLUTIONS AND METHOD TO REMOVE HALIDE IONS FROM LIQUID AQUEOUS SAMPLES

FIELD OF THE INVENTION

The present invention is directed towards an apparatus for eliminating halide ions, for example chloride and other halides, pseudohalides and sulfides from aqueous solutions, because these ions can interfere with subsequent further determinations and a method to remove said undue ions from liquid aqueous samples.

BACKGROUND OF THE INVENTION AND PRIOR ART

The determination of chemical oxygen demand (COD) as specified in DIN 38409 (Parts 41, 43 and 44) is subject to interference by, inter alia, chloride ions, so that these must be removed in analysis of the water under test. According to the DIN protocol, this is performed by mercury.

Removal of chloride by mercury sulfate which has previously been customary in COD analysis has become recognized as a problem, since this compound is classified as highly toxic ($T^+$) according to the German regulation on hazardous substances. For this reason alternatives have been developed which operate without mercury compounds.

U.S. Pat. Nos. 5,667,754 and 5,683,914 disclose removing chloride ions by reaction with pentavalent bismuth ions. The free chlorine released in this method is expelled from the sample.

Test apparatuses for pretreating samples in which COD is to be determined without use of mercury are already commercially available. DIN 38 414-20 relates to the analysis of sewage sludges and water sediments for polychlorinated biphenyls. In this method a freeze-dried sample is extracted with pentane or hexane and interfering minor components are removed from the extract by column chromatography. In order to remove sulfur compounds, the sample is applied to a glass column or another column which contains a bed which is disposed between two membranes and consists of layers of sodium sulfate, silver nitrate/silica gel adsorbent and sodium sulfate disposed one above the other.

The object of the present invention is to provide a simple apparatus which enables halide ions, in particular chloride ions, to be removed from aqueous solutions, so that these do not interfere in subsequent determination of the chemical oxygen demand of water samples.

BRIEF DESCRIPTION OF THE INVENTION

This object of the invention is achieved by an apparatus for eliminating halide ions from aqueous solutions having a hollow cylindrical sample holding chamber, with a front end and an open rear end, the front end has an orifice; and in the vicinity of which is disposed a filter plate that extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a freely movable bed of an adsorbent reacting with halide ions and forming a sparingly soluble compound, which bed fills a part of the sample holding chamber.

The solution includes a method of removing halide ions from aqueous solutions using an apparatus having a hollow cylindrical sample holding chamber, with a front end and an open rear end, the front end has an orifice; and in the vicinity of which is disposed a filter plate that extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a freely movable bed of a charged adsorbent reacting with halide ions forming a sparingly soluble compound, which bed fills a part of the sample holding chamber by the steps: drawing in a water sample through the orifice at the front end of the sample holding chamber into said chamber by moving the plunger towards the rear end of the sample holding chamber, contacting the water sample with the freely moveable bed of the charged adsorbent present in the sample holding chamber by mixing the water sample with the adsorbent and precipitating the halide ions as a sparingly soluble halide compound and expelling the sample essentially free of halide ions from the apparatus by moving the plunger into the sample holding chamber, wherein the precipitated compound is reliably retained by the filter plate.

DETAILED DESCRIPTION OF THE INVENTION

The apparatus for eliminating chloride ions from aqueous solutions having a hollow cylindrical sample holding chamber, with a front end and an open rear end, the front end is formed as a cone tapering towards the end and having an orifice at the tip point of the cone; and in the vicinity of the front end is disposed a filter plate comprising a glass frit and a plastic frit, said filter plate extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a freely movable bed of silver charged silica gel as an adsorbent reacting with chloride ions forming sparingly soluble silver chloride compound, which bed fills, in the dry state, from 5% to 50% of the volume of the sample holding chamber.

The freely moveable bed of the absorbent which is disposed within the sample holding chamber between the filter plate and the plunger and which is reacting with halide ions, such as chloride ions or other halide ions and forming a sparingly soluble compound, is preferably a finely divided support material which is impregnated or charged with silver nitrate. Suitable support materials are, for example, silica gel, pyrogenic silicic acid, Kieselgur, aluminum oxide, aluminum hydroxide, finely divided polyamide. Mixtures of these support materials can also be used. Particularly suitable materials have proved to be silica gels, that is to say dried colloidal silicic acid having loose to dense pore structure and a particle size of 0.06 mm to 2.0 mm, a pore width of 0.006 $\mu$m, and a specific BET surface area of 450 to 550 $m^2$/g. Charging or impregnation can be performed using silver nitrate dissolved in water and subsequent expulsion of the water.

The adsorbent preferably contains from 5% by weight to 50% by weight of silver nitrate.

The water-soluble silver nitrate forms, by the known reaction with chloride ions, sparingly soluble silver chloride (solubility of silver chloride is $1.7 \times 10^{-10}$ mol$^2 \times$liter$^{-2}$), which precipitates out of the liquid sample.

Completely surprisingly, it has been found that a freely movable bed of this charged adsorbent which only fills a part of the sample holding chamber, for example from 5% to 50% of the volume, when the sample chamber is filled with the water sample and the water sample is mixed with the adsorbent, for example by shaking, rotating or other motion, silver chloride precipitates out in a form such that the precipitate is retained by the filter plate when the sample is expelled from the sample holding chamber. If, in contrast, the same adsorbent is disposed as a solid bed in the sample holding chamber or in a separation column, a finely divided precipitation proceeds, so that the precipitate is not retained by customary membranes or filter plates.

The hollow cylindrical sample holding chamber preferably has a volume of 5 ml to 100 ml, very particularly preferably from 5 ml to 50 ml. The wall thickness of the hollow cylinder can be from 0.5 mm to 2.0 mm. The length of the hollow cylinder is preferably from 30 mm to 120 mm.

The wall of the hollow cylindrical sample holding chamber and the optionally present cone at the front end and the bead or flange at the rear end can be made of glass or inert plastic. Suitable plastics are thermoplastics shapeable by injection-molding or compression molding, such as polyolefins, polycarbonate, (meth)acrylic acid-based polymers/copolymers, polyamide.

The plunger and the plunger stem fixed thereto together with the optionally integrated gripper plate are preferably made of inert plastic. The above mentioned plastics for hollow cylinder are also suitable for forming the plunger and the plunger stem fixed thereto.

The cross section of the plunger is slightly smaller than the internal cross section of the hollow cylindrical sample holding chamber, so that the plunger lies liquid-tightly against the internal wall, but is movable to and fro.

Preferably, the plunger stem has an outer diameter which ensures secure guidance of the plunger in the hollow cylinder. The difference between the internal diameter of the hollow cylinder and the outer diameter of the plunger tip can be about 0.1 mm.

The front end of the hollow cylindrical sample holding chamber is preferably formed as a truncated cone which extends towards the front end with the orifice at the point of the cone, in order to facilitate drawing in the sample by moving the plunger by means of the plunger stem from the bed of the adsorbent in the direction of the rear end of the hollow cylinder and, vice versa, to facilitate the expulsion by corresponding counter movement of the plunger.

To facilitate the to and fro movement of the plunger, at the rear end of the hollow cylinder a surrounding bead or an outwardly projecting flange can be present on the outer wall. The flange need not extend over the entire outer periphery of the hollow cylinder, but it can alternatively be present only on two partial regions of the outer periphery which are opposite to one another.

At the rear end of the plunger stem is preferably disposed a gripper plate, whose area is greater than the cross section of the plunger stem, so that the gripper plate projects beyond the plunger stem in at least partial regions.

The filter plate can be a filter made of densely packed fibers, for example glass fibers, inert polymer fibers (for example polyethylene). Plastic frits or glass frits, preferably having pore sizes from 20 $\mu$mm to 200 $\mu$m (micrometer), can also be inserted into the sample holding chamber as filter plate at the front end. Particular preference is given to forming the filter plate from two layers, combining with a fiber filter, for example a glass fiber filter, with a frit, for example an inert plastic frit, the fiber filter being disposed between the frit and the front end of the hollow cylinder, for example a plastic frit with a glass frit the glass frit being disposed between the plastic frit and the front end of the hollow cylinder. Preferably the plastic frit is made of polyolefins such as Polyethylene or Polypropylene.

The inventive apparatus is intended in particular for single use. In order to prevent premature contamination of the adsorbent, the apparatus is sealed by a removable sealing, which is not removed until immediately before use. For example, blister packages of aluminum foils or plastic films.

When a water sample is pretreated, for example for subsequent determination of chemical oxygen demand or other analyses, to remove interfering ions, in particular chloride ions and/or other halide ions, pseudohalide ions and sulfides, the following procedure is followed:

After removing the seal from the apparatus, the water sample is drawn in towards the rear end of the sample holding chamber by moving the plunger. Contact with the adsorbent impregnated with a reaction medium for the ions to be removed from the sample causes ions which interfere in the subsequently intended COD determinations or other analyses to be precipitated out in the form of a sparingly soluble compound having a solubility product less than $10^{-8}$. Precipitation is initiated on contact with the freely movable bed of the adsorbent present in the sample holding chamber, for example with silver-nitrate-impregnated silica gel. By the intensive contact and fine distribution of the adsorbent on mixing in the sample liquid, for example by shaking the apparatus containing the sample taken in, the sparingly soluble compound, for example silver chloride, is precipitated out in a form such that the precipitated compound is reliably retained by the filter plate, which is liquid-permeable, and essentially impermeable to solids, when the sample is expelled from the apparatus. A time of about 30 seconds on mixing, for example by shaking, is generally sufficient for a 5 ml sample to cause the precipitation.

In this manner up to 2000 mg/l of interfering ions such as chloride can be eliminated from about a 5 ml sample. In the case of higher contents of unwanted ions or larger sample amounts, use of a further innovative apparatus can ensure that the unwanted ions are always removed.

In the case of larger samples and correspondingly larger volumes of the sample holding chamber, a longer time may be required for complete precipitation.

BRIEF DESCRIPTION OF THE FIGURE

The FIGURE shows a longitudinal cross section of the device according to the invention.

The invention is described in more detail with reference to an example and the FIGURE which shows diagrammatically a longitudinal section. The apparatus 1 has a hollow cylindrical sample holding chamber 2, the wall of which is made of plastic. At the front end of the hollow cylinder, an orifice 3 is present, through which the water sample to be treated enters into the sample holding chamber 2 and can exit again after the treatment.

The front end of the sample holding chamber 2 is formed as a cone tapering towards the end with the orifice 3 at the point of the cone. The cross section of the hollow cylinder decreases in the transition of the sample holding chamber to the adjoining cone. In the immediate vicinity of the front end of the sample holding chamber 2 is disposed a filter plate 4 which is inserted in a fixed manner into the hollow cylinder, and is liquid-permeable, but is essentially impermeable to solids present in the liquid sample.

From the open rear end 5 of the sample holding chamber 2, a plunger 6 which can move to and fro and has a plunger stem 7 integrated therein engages in the sample holding chamber 2. The cross section of the plunger 6 is slightly less than the inner cross section of the sample holding chamber 2, so that the plunger lies liquid-tightly against the internal wall of the sample holding chamber, but is movable to and fro. The plunger stem 7, when the plunger 6 is pushed in, projects beyond the end 5 of the hollow cylinder. In order to facilitate movement of the plunger stem in use, at the rear end 5 of the hollow cylinder a flange 8 which projects outwards and a gripper plate 9 at the end of the plunger stem are provided. In the sample holding chamber 2 a freely movable bed of an adsorbent which reacts with the unwanted ions, for example chloride ions, is disposed, which bed fills a part of the sample holding chamber.

LIST OF REFERENCE NUMBERS USED IN THE FIGURE

1 Apparatus according to the invention
2 Hollow cylindrical sample holding chamber, hollow cylinder
3 Orifice at the front end of the hollow cylinder
4 Filter plate inserted in a fixed manner
5 Rear end of the hollow cylindrical sample holding chamber, hollow cylinder
6 Plunger
7 Plunger stem
8 flange, surrounding outer bead
9 Gripper plate

What is claimed is:

1. Apparatus for eliminating halide ions from aqueous solutions having a hollow cylindrical sample holding chamber, with a front end and an open rear end, the front end has an orifice; and in the vicinity of which is disposed a filter plate that extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a bed of finely divided particulate adsorbent which particles are freely movable with respect to one another within the sample holding chamber, the adsorbent reacting with halide ions and forming a sparingly soluble compound, which bed fills a part of the sample holding chamber.

2. The apparatus according to claim 1, wherein the adsorbent is finely divided support material charged with silver nitrate.

3. The apparatus according to claim 2, wherein the finely divided support material is selected from silica gel, pyrogenic silicic acid, kieselguhr, aluminum oxide, aluminum hydroxide, finely divided polyamide or mixtures thereof.

4. The apparatus according to claim 1, wherein the adsorbent bed fills, in the dry state, from 5% to 50% of the sample holding chamber.

5. The apparatus according to claim 1, wherein the front end of the hollow cylindrical sample chamber is formed as a cone tapering towards the end having the orifice at the tip of the point of the cone.

6. The apparatus according to claim 5, wherein at the rear end of the sample holding chamber an outwardly projecting flange is present.

7. The apparatus according to claim 5, wherein at the rear end of the sample holding chamber an outer surrounding bead is present.

8. The apparatus according to claim 1, wherein a gripper plate is present at the rear end of the plunger stem.

9. The apparatus according to claim 1, wherein the wall of the hollow cylindrical sample holding chamber is made of glass.

10. The apparatus according to claim 1, wherein the wall of the hollow cylindrical sample holding chamber is made of inert plastic.

11. The apparatus according to claims 1, wherein the plunger and the plunger stem are made of inert plastic.

12. The apparatus according to claim 1, wherein the filter plate is made of a material selected from densely packed glass fibers, a plastic frit, a glass frit, or combinations thereof.

13. The apparatus according to claim 12, wherein the filter plate is a combination of a plastic frit with densely packed glass fibers, the glass fibers being disposed between the plastic frit and the front end of the hollow cylindrical sample holding chamber.

14. The apparatus according to claim 12, wherein the filter plate is a combination of a glass frit with densely packed glass fibers, the glass fibers being disposed between the glass frit and the front end of the hollow cylindrical sample holding chamber.

15. The apparatus according to claim 12, wherein the filter plate is a combination of a glass frit with a plastic frit, the glass frit being disposed between the plastic frit and the front end of the hollow cylindrical sample holding chamber.

16. The apparatus according to claim 12, wherein the plastic frit used for the filter plate has a pore size of from 20 $\mu$mm to 200 $\mu$m.

17. The apparatus according to claim 12, wherein glass frit used for the filter plate has a pore size of from 20 $\mu$m to 200 $\mu$m.

18. An apparatus for eliminating chloride ions from aqueous solutions having a hollow cylindrical sample holding chamber, with a front end and an open rear end, the front end is formed as a cone tapering towards the end and having an orifice at the tip point of the cone; and in the vicinity of the front end is disposed a filter plate comprising a glass frit and a plastic frit, said filter plate extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a bed of finely divided particulate silver charged silica gel as an adsorbent which particles are freely movable with respect to one another within the sample holding chamber, the adsorbent reacting with chloride ions forming sparingly soluble silver chloride compound, which bed fills, in the dry state, from 5% to 50% of the volume of the sample holding chamber.

19. A method of removing halide ions from aqueous solutions using an apparatus having a hollow cylindrical sample holding chamber, with a front end and an open rear end, the front end has an orifice; and in the vicinity of which is disposed a filter plate that extends over the cross section of the sample holding chamber and is liquid-permeable and essentially impermeable for solids and is inserted in a fixed manner into the hollow cylindrical sample holding chamber; a plunger which can move to and fro in the sample holding chamber and having a plunger stem which engages in the open rear end of the sample holding chamber, and, in the sample holding chamber between the filter plate and the plunger is disposed a bed of a charged finely divided particulate adsorbent which particles are freely movable with respect to one another within the sample holding chamber, the adsorbent reacting with halide ions forming a sparingly soluble compound, which bed fills a part of the sample holding chamber by the steps:

drawing in a water sample through the orifice at the front end of the sample holding chamber into said chamber by moving the plunger towards the rear end of the sample holding chamber, contacting the water sample with the bed of the charged adsorbent present in the sample holding chamber by mixing the water sample with the adsorbent and precipitating the halide ions as a sparingly soluble halide compound and expelling the sample essentially free of halide ions from the apparatus by moving the plunger into the sample holding chamber, wherein the precipitated compound is reliably retained by the filter plate.

20. The method according to claim 19, wherein the adsorbent is silica gel charged with silver nitrate and the sparingly soluble halide compound is silver halide.

21. The method according to claim 19, wherein the halide ion is chloride and the sparingly soluble halide compound is silver chloride.

* * * * *